United States Patent [19]

Meola

[11] Patent Number: 4,783,449
[45] Date of Patent: Nov. 8, 1988

[54] HYDROSOLUBLE PHARMACEUTICAL COMPOSITIONS CONTAINING SALTS OF (−)CIS-1,2-EPOXYPROPYLPHOSPHONIC ACID WITH AMINOACIDS

[75] Inventor: Stefania Meola, Milan, Italy

[73] Assignee: Istituto Gentili S.p.A., Pisa, Italy

[21] Appl. No.: 783,747

[22] Filed: Oct. 3, 1985

[30] Foreign Application Priority Data

Oct. 5, 1984 [CH] Switzerland .................. 4791/84

[51] Int. Cl.$^4$ .................. A61K 31/685; A61K 31/665
[52] U.S. Cl. ........................... 514/76; 514/99; 514/970
[58] Field of Search ............ 514/99, 76, 970, 946, 514/947

[56] References Cited

U.S. PATENT DOCUMENTS 4,581,360 4/1986 Ottenheijm .................. 514/274

FOREIGN PATENT DOCUMENTS 2820794 5/1979 Fed. Rep. of Germany ........ 514/99

OTHER PUBLICATIONS

The Merck Index, 10th ed., 1983, p. 63, No. 429.

Primary Examiner—Albert T. Meyers
Assistant Examiner—Richard Kearse
Attorney, Agent, or Firm—Walter H. Schneider

[57] ABSTRACT

Hydrosoluble pharmaceutical compositions containing, as the active principal, salts of (−)cis-1,2-epoxypropylphosphonic acid with aminoacids such as arginine, ornithine, lysine, cysteine, and the like, characterized by containing a hydrophyllic organic base.

2 Claims, No Drawings

HYDROSOLUBLE PHARMACEUTICAL COMPOSITIONS CONTAINING SALTS OF (−)CIS-1,2-EPOXYPROPYLPHOSPHONIC ACID WITH AMINOACIDS

The present invention refers to pharmaceutical compositions having antibiotic activity, which can be administered by the parenteral route in the form of a solution.

In the Italian Patent Applications Nos. 41002 A/78 and 26304 A/78 salts having formula I are described

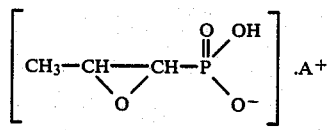

wherein A is an aminoacid, such as lysine, arginine, ornithine, cysteine, methionine, glycine, choline, alanine, betaine, etc. whereas the anionic moiety is provided by (−)cis-1,2-epoxypropylphosphonic acid, compound known also as phosphomycin and used in human and veterinary therapy because of its antibiotic properties.

Particularly, the phosphomycin arginine salt proved to be endowed with unexpected and advantageous therapeutic properties.

The compounds I, according to the processes described in said patent applications, are prepared by reacting substantially equimolar amounts of (−)cis-1,2-epoxypropylphosphonic acid and of aminoacid, preferably in aqueous solution, or in hydroalcoholic solution with methyl or ethyl alcohol.

The compounds so obtained proved, however, to be not very soluble, so as to make problematic their parenteral administration (especially endovenous) in form of solutions. On the other hand, said administration routes are very frequent in the clinical practice for antibiotic therapies.

It has now been found that compounds I, and namely the compound I wherein A represents arginine, can be suitably formulated in hydrosoluble compositions, having a water solubility ranging from 10 and 20% w/v, by adding a suitable amount of hydrophilic organic bases either during the preparation of said salts or directly before the final conditioning in pharmaceutical forms.

The base is preferably added in a molar ratio ranging from about 0.4 to about 0.8, and even more preferably about 0.6.

Preferred hydropholic organic bases are 1,1-dimethyl-2-aminoethanol, 2-aminobutanol, 2-amino-2-hydroxymethyl-1,3-propandiol and, generally, similar compounds belonging to the class of the aminoalcohols.

The pH of the solutions obtained according to the invention are in the range of physiologically acceptable values, namely from about 6.9 to 7.4.

As already mentioned, the phosphomycin formulations according to the present invention, obtained by salification with aminoacids and with the above organic bases, belonging to the class of the aminoalcohols, are characterized by a high water solubility, higher than that of similar salts, and by the possibility to obtain, even by the oral administration, higher and more prolonged blood levels of the antibiotic in its active form.

Moreover, the compositions according to the invention—in comparison with other phosphomycin salts—exhibit an higher tropism for some organs, such as lungs and kidneys.

On the other hand, the favourable toxicological characteristics of phosphomycin as well as its wide antibacterial spectrum are not in any way compromised.

The injectable pharmaceutical preparations according to the present invention may comprise obviously other suitable excipients, whose use is conventional and well known to the persons skilled in the art: similarly known are the sterility, apirogenicity and isotonicity conditions which must be met by said compositions for the foreseen use.

According to the invention, it is also possible to prepare liquid oral pharmaceutical compositions such as syrups, drinkable solutions, effervescent powders etc.

In the case of parenteral administration, the compositions of the invention will contain from 0.1 to 0.5 g of the active principle, and from 0.5 to 1 g of the active principle in the case of oral administration.

The daily posology will depend, of course, on the diagnosis, the patient's gravity, age and weight.

In the following table, reported by way of non-limitative example, the hydrosoluble organic bases used in the respective amounts and the obtained solubility and pH results are reported.

TABLE

Compositions containing phosphomycin arginine salt (1:1) with hydrophilic organic bases.

| Organic base | Molar ratio | Solubility g % | pH |
|---|---|---|---|
| $\begin{array}{c} CH_3 \\ \| \\ H_2NH_2CCOH \\ \| \\ CH_3 \end{array}$ | 0.5 | 18 | 6.9 |
| $\begin{array}{c} CH_3CH_2CHCH_2OH \\ \| \\ NH_2 \end{array}$ | 0.56 | 15 | 6.82 |
| $\begin{array}{c} CH_2OH \\ \| \\ H_2NCCH_2OH \\ \| \\ CH_2OH \end{array}$ | 0.55 | 14 | 6.93 |

I claim:

1. A pharmaceutical composition having antibiotic properties comprising a salt of (−)cis-1,2-epoxypropylphosphonic acid with arginine together with an aminoalcohol selected from the group consisting of 1,1-dimethyl-2-aminoethanol, 2-aminobutanol and 2-amino-2-hydroxymethyl-1,3-propandiol in a molar ratio of 0.4–0.8 to increase the water solubility of said salt.

2. A composition according to claim 1 in which the amino-alcohol is present in a molar ratio of about 0.6.